(12) United States Patent
Ameri (10) Patent No.: US 8,160,717 B2
(45) Date of Patent: Apr. 17, 2012

(54) MODEL REFERENCE IDENTIFICATION AND CANCELLATION OF MAGNETICALLY-INDUCED VOLTAGES IN A GRADIENT MAGNETIC FIELD

(75) Inventor: Masoud Ameri, Maple Plain, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 521 days.

(21) Appl. No.: 12/368,752

(22) Filed: Feb. 10, 2009

(65) Prior Publication Data

US 2009/0210025 A1 Aug. 20, 2009

Related U.S. Application Data

(60) Provisional application No. 61/029,743, filed on Feb. 19, 2008.

(51) Int. Cl.
*A61N 1/08* (2006.01)
(52) U.S. Cl. ........................................................ 607/63
(58) Field of Classification Search ..................... 607/62
See application file for complete search history.

(56) References Cited

U.S. PATENT DOCUMENTS

| | | | |
|---|---|---|---|
| 3,888,260 A | 6/1975 | Fischell | |
| 3,898,995 A | 8/1975 | Dresbach | |
| 4,091,818 A | 5/1978 | Brownlee et al. | |
| 4,379,459 A | 4/1983 | Stein | |
| 4,404,125 A | 9/1983 | Abolins et al. | |
| 4,516,579 A | 5/1985 | Irnich | |
| 4,611,127 A | 9/1986 | Ibrahim et al. | |
| 4,694,837 A | 9/1987 | Blakeley et al. | |
| 4,729,376 A | 3/1988 | DeCote, Jr. | |
| 4,751,110 A | 6/1988 | Gulla et al. | |
| 4,779,617 A | 10/1988 | Whigham | |
| 4,823,075 A | 4/1989 | Alley | |
| 4,869,970 A | 9/1989 | Gulla et al. | |
| 4,934,366 A | 6/1990 | Truex et al. | |
| 5,038,785 A | 8/1991 | Blakeley et al. | |
| 5,075,039 A | 12/1991 | Goldberg | |
| 5,076,841 A | 12/1991 | Chen et al. | |
| 5,120,578 A | 6/1992 | Chen et al. | |
| 5,187,136 A | 2/1993 | Klobucar et al. | |
| 5,188,117 A | 2/1993 | Steinhaus et al. | |

(Continued)

FOREIGN PATENT DOCUMENTS

EP 0 530 006 3/1993

(Continued)

OTHER PUBLICATIONS

Kerr, Martha, Shock Rate Cut 70% With ICDs Programmed to First Deliver Antitachycardia Pacing: Results of the PainFREE Rx II Trial, Medscape CRM News, May 21, 2003.

(Continued)

*Primary Examiner* — Michael Kahelin
(74) *Attorney, Agent, or Firm* — Faegre Bakers Daniels LLP (57) ABSTRACT

Systems and methods of dynamically controlling an implanted medical device located within a patient's body in the presence of a gradient magnetic field or other external interference are disclosed. The system can include a reference model of the implanted medical device and of body tissue within the patient's body in the absence of a gradient magnetic field, and a control unit configured to dynamically control voltages or currents applied to a lead of the implanted medical device based on predicted parameters determined by the reference model.

19 Claims, 5 Drawing Sheets

U.S. PATENT DOCUMENTS

| | | |
|---|---|---|
| 5,197,468 A | 3/1993 | Proctor et al. |
| 5,217,010 A | 6/1993 | Tsitlik et al. |
| 5,243,911 A | 9/1993 | Dow et al. |
| 5,279,225 A | 1/1994 | Dow et al. |
| 5,288,313 A | 2/1994 | Portner |
| 5,292,342 A | 3/1994 | Nelson et al. |
| 5,309,096 A | 5/1994 | Hoegnelid |
| 5,325,728 A | 7/1994 | Zimmerman et al. |
| 5,345,362 A | 9/1994 | Winkler |
| 5,391,188 A | 2/1995 | Nelson et al. |
| 5,406,444 A | 4/1995 | Selfried et al. |
| 5,424,642 A | 6/1995 | Ekwall |
| 5,438,990 A | 8/1995 | Wahlstrand et al. |
| 5,454,837 A | 10/1995 | Lindegren et al. |
| 5,470,345 A | 11/1995 | Hassler et al. |
| 5,523,578 A | 6/1996 | Herskovic |
| 5,527,348 A | 6/1996 | Winkler et al. |
| 5,529,578 A | 6/1996 | Struble |
| 5,545,187 A | 8/1996 | Bergstrom et al. |
| 5,562,714 A | 10/1996 | Grevious |
| 5,607,458 A | 3/1997 | Causey, III et al. |
| 5,609,622 A | 3/1997 | Soukrup et al. |
| 5,618,208 A | 4/1997 | Crouse et al. |
| 5,620,476 A | 4/1997 | Truex et al. |
| 5,647,379 A | 7/1997 | Meltzer |
| 5,649,965 A | 7/1997 | Pons et al. |
| 5,650,759 A | 7/1997 | Hittman et al. |
| 5,662,694 A | 9/1997 | Lidman et al. |
| 5,683,434 A | 11/1997 | Archer |
| 5,687,735 A | 11/1997 | Forbes et al. |
| 5,694,952 A | 12/1997 | Lidman et al. |
| 5,697,958 A | 12/1997 | Paul et al. |
| 5,709,225 A | 1/1998 | Budgifvars et al. |
| 5,714,536 A | 2/1998 | Ziolo et al. |
| 5,722,998 A | 3/1998 | Prutchi et al. |
| 5,727,552 A | 3/1998 | Ryan |
| 5,735,884 A | 4/1998 | Thompson et al. |
| 5,749,910 A | 5/1998 | Brumwell et al. |
| 5,751,539 A | 5/1998 | Stevenson et al. |
| 5,759,197 A | 6/1998 | Sawchuk et al. |
| 5,764,052 A | 6/1998 | Renger |
| 5,766,227 A | 6/1998 | Nappholz et al. |
| 5,776,168 A | 7/1998 | Gunderson |
| 5,782,891 A | 7/1998 | Hassler et al. |
| 5,792,201 A | 8/1998 | Causey, III et al. |
| 5,800,496 A | 9/1998 | Swoyer et al. |
| 5,800,497 A | 9/1998 | Bakels et al. |
| 5,814,090 A | 9/1998 | Latterell et al. |
| 5,817,130 A | 10/1998 | Cox et al. |
| 5,827,997 A | 10/1998 | Chung et al. |
| 5,853,375 A | 12/1998 | Orr |
| 5,867,361 A | 2/1999 | Wolf et al. |
| 5,869,078 A | 2/1999 | Baudino |
| 5,870,272 A | 2/1999 | Seifried et al. |
| 5,871,509 A | 2/1999 | Noren |
| 5,877,630 A | 3/1999 | Kraz |
| 5,895,980 A | 4/1999 | Thompson |
| 5,905,627 A | 5/1999 | Brendel et al. |
| 5,959,829 A | 9/1999 | Stevenson et al. |
| 5,964,705 A | 10/1999 | Truwit et al. |
| 5,968,854 A | 10/1999 | Akopian et al. |
| 5,973,906 A | 10/1999 | Stevenson et al. |
| 5,978,204 A | 11/1999 | Stevenson |
| 5,978,710 A | 11/1999 | Prutchi et al. |
| 5,999,398 A | 12/1999 | Makl et al. |
| 6,008,980 A | 12/1999 | Stevenson et al. |
| 6,031,710 A | 2/2000 | Wolf et al. |
| 6,032,063 A | 2/2000 | Hoar et al. |
| 6,055,455 A | 4/2000 | O'Phelan et al. |
| 6,079,681 A | 6/2000 | Stern et al. |
| 6,101,417 A | 8/2000 | Vogel et al. |
| 6,147,301 A | 11/2000 | Bhatia |
| 6,161,046 A | 12/2000 | Maniglia et al. |
| 6,162,180 A | 12/2000 | Miesel et al. |
| 6,173,203 B1 | 1/2001 | Barkley et al. |
| 6,188,926 B1 | 2/2001 | Vock |
| 6,192,279 B1 | 2/2001 | Barreras, Sr. et al. |
| 6,198,968 B1 | 3/2001 | Prutchi et al. |
| 6,198,972 B1 | 3/2001 | Hartlaub et al. |
| 6,209,764 B1 | 4/2001 | Hartlaub et al. |
| 6,217,800 B1 | 4/2001 | Hayward |
| 6,235,038 B1 | 5/2001 | Hunter et al. |
| 6,245,464 B1 | 6/2001 | Spillman et al. |
| 6,246,902 B1 | 6/2001 | Naylor et al. |
| 6,249,701 B1 | 6/2001 | Rajasekhar et al. |
| 6,268,725 B1 | 7/2001 | Vernon et al. |
| 3,275,369 A1 | 8/2001 | Stevenson et al. |
| 6,270,831 B2 | 8/2001 | Kumar et al. |
| 6,275,369 B1 | 8/2001 | Stevenson et al. |
| 6,288,344 B1 | 9/2001 | Youker et al. |
| 6,324,431 B1 | 11/2001 | Zarinetchi et al. |
| 6,358,281 B1 | 3/2002 | Berrang et al. |
| 6,365,076 B1 | 4/2002 | Bhatia |
| 6,381,494 B1 | 4/2002 | Gilkerson et al. |
| 6,421,555 B1 | 7/2002 | Nappoholz |
| 6,424,234 B1 | 7/2002 | Stevenson |
| 6,446,512 B2 | 9/2002 | Zimmerman et al. |
| 6,452,564 B1 | 9/2002 | Schoen et al. |
| 6,456,481 B1 | 9/2002 | Stevenson |
| 6,459,935 B1 | 10/2002 | Piersma |
| 6,470,212 B1 | 10/2002 | Weijand et al. |
| 6,487,452 B2 | 11/2002 | Legay |
| 6,490,148 B1 | 12/2002 | Allen et al. |
| 6,496,714 B1 | 12/2002 | Weiss et al. |
| 6,503,964 B2 | 1/2003 | Smith et al. |
| 6,506,972 B1 | 1/2003 | Wang |
| 6,510,345 B1 | 1/2003 | Van Bentem |
| 6,512,666 B1 | 1/2003 | Duva |
| 6,522,920 B2 | 2/2003 | Silvian et al. |
| 6,526,321 B1 | 2/2003 | Spher |
| 6,539,253 B2 | 3/2003 | Thompson et al. |
| 6,545,854 B2 | 4/2003 | Trinh et al. |
| 6,555,745 B1 | 4/2003 | Kruse et al. |
| 6,563,132 B1 | 5/2003 | Talroze et al. |
| 6,566,978 B2 | 5/2003 | Stevenson et al. |
| 6,567,259 B2 | 5/2003 | Stevenson et al. |
| 6,580,947 B1 | 6/2003 | Thompson |
| 6,584,351 B1 | 6/2003 | Ekwall |
| 6,595,756 B2 | 7/2003 | Gray et al. |
| 6,607,485 B2 | 8/2003 | Bardy |
| 6,626,937 B1 | 9/2003 | Cox |
| 6,629,938 B1 | 10/2003 | Engvall |
| 6,631,290 B1 | 10/2003 | Guck et al. |
| 6,631,555 B1 | 10/2003 | Youker et al. |
| 6,640,137 B2 | 10/2003 | MacDonald |
| 6,643,903 B2 | 11/2003 | Stevenson et al. |
| 6,646,198 B2 | 11/2003 | Maciver et al. |
| 6,648,914 B2 | 11/2003 | Berrang et al. |
| 6,662,049 B1 | 12/2003 | Miller |
| 6,673,999 B1 | 1/2004 | Wang et al. |
| 6,711,440 B2 | 3/2004 | Deal et al. |
| 6,713,671 B1 | 3/2004 | Wang et al. |
| 6,718,203 B2 | 4/2004 | Weiner et al. |
| 6,718,207 B2 | 4/2004 | Connelly |
| 6,725,092 B2 | 4/2004 | MacDonald et al. |
| 6,731,979 B2 | 5/2004 | MacDonald |
| 6,795,730 B2 | 9/2004 | Connelly et al. |
| 6,901,292 B2 | 5/2005 | Hrdlicka et al. |
| 6,925,328 B2 | 8/2005 | Foster et al. |
| 6,937,906 B2 | 8/2005 | Terry et al. |
| 6,944,489 B2 | 9/2005 | Zeijlemaker et al. |
| 6,963,779 B1 | 11/2005 | Shankar |
| 7,013,180 B2 | 3/2006 | Villaseca et al. |
| 7,050,855 B2 | 5/2006 | Zeijlemaker et al. |
| 7,076,283 B2 | 7/2006 | Cho et al. |
| 7,082,328 B2 | 7/2006 | Funke |
| 7,092,756 B2 | 8/2006 | Zhang et al. |
| 7,123,013 B2 | 10/2006 | Gray |
| 7,138,582 B2 | 11/2006 | Lessar et al. |
| 7,164,950 B2 | 1/2007 | Kroll et al. |
| 7,174,219 B2 | 2/2007 | Wahlstrand et al. |
| 7,174,220 B1 | 2/2007 | Chitre et al. |
| 7,212,863 B2 | 5/2007 | Strandberg |
| 7,231,251 B2 | 6/2007 | Yonce et al. |
| 7,242,981 B2 | 7/2007 | Ginggen |
| 7,272,444 B2 | 9/2007 | Peterson et al. |
| 7,369,898 B1 | 5/2008 | Kroll et al. |

| | | |
|---|---|---|
| 7,388,378 B2 | 6/2008 | Gray et al. |
| 7,509,167 B2 | 3/2009 | Stessman |
| 7,561,915 B1 | 7/2009 | Cooke et al. |
| 7,835,803 B1 | 11/2010 | Malinowski et al. |
| 7,839,146 B2 | 11/2010 | Gray |
| 2001/0002000 A1 | 5/2001 | Kumar et al. |
| 2001/0006263 A1 | 7/2001 | Hayward |
| 2001/0011175 A1 | 8/2001 | Hunter et al. |
| 2001/0018123 A1 | 8/2001 | Furumori et al. |
| 2001/0025139 A1 | 9/2001 | Pearlman |
| 2001/0037134 A1 | 11/2001 | Munshi |
| 2001/0050837 A1 | 12/2001 | Stevenson et al. |
| 2002/0019658 A1 | 2/2002 | Munshi |
| 2002/0026224 A1 | 2/2002 | Thompson et al. |
| 2002/0038135 A1 | 3/2002 | Connelly et al. |
| 2002/0050401 A1 | 5/2002 | Youker et al. |
| 2002/0072769 A1 | 6/2002 | Silvian et al. |
| 2002/0082648 A1 | 6/2002 | Kramer et al. |
| 2002/0102835 A1 | 8/2002 | Stucchi et al. |
| 2002/0116028 A1 | 8/2002 | Greatbatch et al. |
| 2002/0116029 A1 | 8/2002 | Miller et al. |
| 2002/0116033 A1 | 8/2002 | Greatbatch et al. |
| 2002/0116034 A1 | 8/2002 | Miller et al. |
| 2002/0117314 A1 | 8/2002 | Maciver et al. |
| 2002/0128689 A1 | 9/2002 | Connelly et al. |
| 2002/0128691 A1 | 9/2002 | Connelly |
| 2002/0133086 A1 | 9/2002 | Connelly et al. |
| 2002/0133199 A1 | 9/2002 | MacDonald et al. |
| 2002/0133200 A1 | 9/2002 | Weiner et al. |
| 2002/0133201 A1 | 9/2002 | Connelly et al. |
| 2002/0133202 A1 | 9/2002 | Connelly et al. |
| 2002/0133208 A1 | 9/2002 | Connelly |
| 2002/0133211 A1 | 9/2002 | Weiner et al. |
| 2002/0133216 A1 | 9/2002 | Connelly et al. |
| 2002/0138102 A1 | 9/2002 | Weiner et al. |
| 2002/0138107 A1 | 9/2002 | Weiner et al. |
| 2002/0138108 A1 | 9/2002 | Weiner et al. |
| 2002/0138110 A1 | 9/2002 | Connelly et al. |
| 2002/0138112 A1 | 9/2002 | Connelly et al. |
| 2002/0138113 A1 | 9/2002 | Connelly et al. |
| 2002/0138124 A1 | 9/2002 | Helfer et al. |
| 2002/0143258 A1 | 10/2002 | Weiner et al. |
| 2002/0147388 A1 | 10/2002 | Mass et al. |
| 2002/0147470 A1 | 10/2002 | Weiner et al. |
| 2002/0162605 A1 | 11/2002 | Horton, Jr. et al. |
| 2002/0166618 A1 | 11/2002 | Wolf et al. |
| 2002/0175782 A1 | 11/2002 | Trinh et al. |
| 2002/0183796 A1 | 12/2002 | Connelly |
| 2002/0198569 A1 | 12/2002 | Foster et al. |
| 2003/0036774 A1 | 2/2003 | Maier et al. |
| 2003/0036776 A1 | 2/2003 | Foster et al. |
| 2003/0045907 A1 | 3/2003 | MacDonald |
| 2003/0053284 A1 | 3/2003 | Stevenson et al. |
| 2003/0055457 A1 | 3/2003 | MacDonald |
| 2003/0056820 A1 | 3/2003 | MacDonald |
| 2003/0074029 A1 | 4/2003 | Deno et al. |
| 2003/0081370 A1 | 5/2003 | Haskell et al. |
| 2003/0083570 A1 | 5/2003 | Cho et al. |
| 2003/0083723 A1 | 5/2003 | Wilkinson et al. |
| 2003/0083726 A1 | 5/2003 | Zeijlemaker et al. |
| 2003/0083728 A1 | 5/2003 | Greatbatch et al. |
| 2003/0100925 A1 | 5/2003 | Pape et al. |
| 2003/0109901 A1 | 6/2003 | Greatbatch |
| 2003/0111142 A1 | 6/2003 | Horton, Jr. et al. |
| 2003/0114897 A1 | 6/2003 | Von Arx et al. |
| 2003/0114898 A1 | 6/2003 | Von Arx et al. |
| 2003/0120197 A1 | 6/2003 | Kaneko et al. |
| 2003/0130647 A1 | 7/2003 | Gray et al. |
| 2003/0130700 A1 | 7/2003 | Miller et al. |
| 2003/0130701 A1 | 7/2003 | Miller |
| 2003/0130708 A1 | 7/2003 | Von Arx et al. |
| 2003/0135114 A1 | 7/2003 | Pacetti |
| 2003/0135160 A1 | 7/2003 | Gray et al. |
| 2003/0139096 A1 | 7/2003 | Stevenson et al. |
| 2003/0140931 A1 | 7/2003 | Zeijlemaker et al. |
| 2003/0144704 A1 | 7/2003 | Terry et al. |
| 2003/0144705 A1 | 7/2003 | Funke |
| 2003/0144706 A1 | 7/2003 | Funke |
| 2003/0144716 A1 | 7/2003 | Reinke et al. |
| 2003/0144717 A1 | 7/2003 | Hagele |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0149459 A1 | 8/2003 | Von Arx et al. |
| 2003/0158584 A1 | 8/2003 | Cates et al. |
| 2003/0176900 A1 | 9/2003 | MacDonald |
| 2003/0179536 A1 | 9/2003 | Stevenson et al. |
| 2003/0191505 A1 | 10/2003 | Gryzwa et al. |
| 2003/0195570 A1 | 10/2003 | Deal et al. |
| 2003/0199755 A1 | 10/2003 | Halperin et al. |
| 2003/0204207 A1 | 10/2003 | MacDonald et al. |
| 2003/0204215 A1 | 10/2003 | Gunderson et al. |
| 2003/0204217 A1 | 10/2003 | Greatbatch |
| 2003/0213604 A1 | 11/2003 | Stevenson et al. |
| 2003/0213605 A1 | 11/2003 | Brendel et al. |
| 2004/0005483 A1 | 1/2004 | Lin |
| 2004/0015162 A1 | 1/2004 | McGaffigan |
| 2004/0015197 A1 | 1/2004 | Gunderson |
| 2004/0019273 A1 | 1/2004 | Helfer et al. |
| 2004/0049237 A1* | 3/2004 | Larson et al. .................... 607/17 |
| 2004/0088012 A1 | 5/2004 | Kroll et al. |
| 2004/0093432 A1 | 5/2004 | Luo et al. |
| 2004/0263174 A1 | 12/2004 | Gray et al. |
| 2005/0070975 A1 | 3/2005 | Zeijlemaker et al. |
| 2005/0113676 A1 | 5/2005 | Weiner et al. |
| 2005/0113873 A1 | 5/2005 | Weiner et al. |
| 2005/0113876 A1 | 5/2005 | Weiner et al. |
| 2005/0197677 A1 | 9/2005 | Stevenson |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2006/0025820 A1 | 2/2006 | Phillips et al. |
| 2006/0030774 A1 | 2/2006 | Gray et al. |
| 2006/0041294 A1 | 2/2006 | Gray |
| 2006/0167496 A1 | 7/2006 | Nelson et al. |
| 2006/0247747 A1 | 11/2006 | Olsen et al. |
| 2006/0247748 A1 | 11/2006 | Wahlstrand et al. |
| 2006/0271138 A1 | 11/2006 | MacDonald |
| 2006/0293591 A1 | 12/2006 | Wahlstrand et al. |
| 2007/0021814 A1 | 1/2007 | Inman et al. |
| 2007/0179577 A1 | 8/2007 | Marshall et al. |
| 2007/0179582 A1 | 8/2007 | Marshall et al. |
| 2007/0191914 A1 | 8/2007 | Stessman |
| 2007/0203523 A1 | 8/2007 | Betzold |
| 2007/0238975 A1 | 10/2007 | Zeijlemaker |
| 2007/0255332 A1 | 11/2007 | Cabelka et al. |
| 2008/0033497 A1 | 2/2008 | Bulkes et al. |
| 2008/0132985 A1 | 6/2008 | Wedan et al. |
| 2008/0221638 A1 | 9/2008 | Wedan et al. |
| 2009/0138058 A1 | 5/2009 | Cooke et al. |
| 2009/0149906 A1 | 6/2009 | Ameri et al. |
| 2009/0149909 A1 | 6/2009 | Ameri |
| 2009/0204182 A1 | 8/2009 | Ameri |
| 2010/0087892 A1 | 4/2010 | Stubbs et al. |
| 2010/0211123 A1 | 8/2010 | Stubbs et al. |
| 2011/0270338 A1 | 11/2011 | Cooke et al. |
| 2011/0276104 A1 | 11/2011 | Ameri et al. |

FOREIGN PATENT DOCUMENTS

| | | |
|---|---|---|
| EP | 0 591 334 | 4/1994 |
| EP | 0 705 621 | 4/1996 |
| EP | 0 719 570 | 7/1996 |
| EP | 0 836 413 | 4/1998 |
| EP | 0 331 959 | 9/1998 |
| EP | 0 870 517 | 10/1998 |
| EP | 0 891 207 | 1/1999 |
| EP | 0 891 786 | 1/1999 |
| EP | 0 980 105 | 2/2000 |
| EP | 0 989 623 | 3/2000 |
| EP | 0 989 624 | 3/2000 |
| EP | 1 007 132 | 6/2000 |
| EP | 1 007 140 | 6/2000 |
| EP | 1 060 762 | 12/2000 |
| EP | 1 061 849 | 12/2000 |
| EP | 1 109 180 | 6/2001 |
| EP | 1 128 764 | 9/2001 |

| | | |
|---|---|---|
| EP | 1 191 556 | 3/2002 |
| EP | 1 271 579 | 1/2003 |
| EP | 1 308 971 | 5/2003 |
| EP | 1 372 782 | 1/2004 |
| WO | WO 91/04069 | 4/1991 |
| WO | WO 96/38200 | 12/1996 |
| WO | WO 97/12645 | 4/1997 |
| WO | WO 00/54953 | 9/2000 |
| WO | WO 01/37286 | 5/2001 |
| WO | WO 01/80940 | 11/2001 |
| WO | WO 01/86774 | 11/2001 |
| WO | WO 02/056761 | 7/2002 |
| WO | WO 02/065895 | 8/2002 |
| WO | WO 02/072004 | 9/2002 |
| WO | WO 02/089665 | 11/2002 |
| WO | WO 02/092161 | 11/2002 |
| WO | WO 03/013199 | 2/2003 |
| WO | WO 03/037399 | 5/2003 |
| WO | WO 03/059445 | 7/2003 |
| WO | WO 03/061755 | 7/2003 |
| WO | WO 03/063946 | 8/2003 |
| WO | WO 03/063952 | 8/2003 |
| WO | WO 03/063954 | 8/2003 |
| WO | WO 03/063955 | 8/2003 |
| WO | WO 03/063956 | 8/2003 |
| WO | WO 03/063958 | 8/2003 |
| WO | WO 03/063962 | 8/2003 |
| WO | WO 03/070098 | 8/2003 |
| WO | WO 03/073449 | 9/2003 |
| WO | WO 03/073450 | 9/2003 |
| WO | WO 03/086538 | 10/2003 |
| WO | WO 03/090846 | 11/2003 |
| WO | WO 03/090854 | 11/2003 |
| WO | WO 03/095022 | 11/2003 |
| WO | WO 2006/124481 | 11/2006 |

OTHER PUBLICATIONS

Schueler et al., "MRI Compatibility and Visibility Assessment of Implantable Medical Devices", *Journal of Magnetic Resonance Imaging*, 9:596-603 (1999).

Sweeney, Michael O. et al., Appropriate and Inappropriate Ventricular Therapies, Quality of Life, and Mortality Among Primary and Secondary Prevention Implantable Cardioverter Defibrillator Patients: Results From the Pacing Fast VT Reduces Shock Therapies (PainFREE Rx II) Trial, American Heart Association, 2005.

Wilkoff, Bruce L. et al., "A Comparison of Empiric to Physician-Tailored Programming of Implantable Cardioverter-Defibrillators Results From the Prospective Randomized Multicenter EMPIRIC Trial," Journal of the American College of Cardiology, vol. 48, No. 2, 2006. doi:10.1016/j.jacc.2006.03.037.

Dempsey Mary F. et al., "Investigation of the Factors Responsible for Burns During MRI", *Journal of Magnetic Resonance Imaging* 2001;13:627-631.

Luechinger, Roger et al., "In vivo heating of pacemaker leads during magnetic resonance imaging", *European Heart Journal* 2005;26:376-383.

Shellock, Frank G. et al., "Cardiovascular catheters and accessories: ex vivo testing of ferromagnetism, heating, and artifacts associated with MRI", *Journal of Magnetic Resonance Imaging*, Nov./Dec. 1998; 8:1338-1342.

Shellock FG, "Reference manual for magnetic resonance safety, implants, and devices", pp. 136-139, 2008 ed. Los Angeles; Biomedical Research Publishing Group; 2008.

International Search Report and Written Opinion issued in PCT/US2009/068314, mailed Mar. 25, 2009, 14 pages.

* cited by examiner

Fig. 5

MODEL REFERENCE IDENTIFICATION AND CANCELLATION OF MAGNETICALLY-INDUCED VOLTAGES IN A GRADIENT MAGNETIC FIELD

CROSS-REFERENCE TO RELATED APPLICATION

This application claims priority under 35 U.S.C. §119 to U.S. Provisional Application No. 61/029,743, filed on Feb. 19, 2008, entitled "Model Reference Identification and Cancellation Of Magnetically-Induced Voltages In A Gradient Magnetic Field," which is incorporated herein by reference in its entirety.

TECHNICAL FIELD

The present invention relates generally to implantable medical devices and the delivery of diagnostic and therapeutic treatments during medical procedures such as magnetic resonance imaging (MRI). More specifically, the present invention relates to the identification and cancellation of magnetically-induced voltages in a gradient magnetic field or other external noise.

BACKGROUND

Magnetic resonance imaging (MRI) is a non-invasive imaging method that utilizes nuclear magnetic resonance techniques to render images within a patient's body. Typically, MRI systems employ the use of a static magnetic coil having a magnetic field strength of between about 0.2 to 3 Teslas. During the procedure, the body tissue is briefly exposed to RF pulses of electromagnetic energy in a plane perpendicular to the magnetic field. The resultant electromagnetic energy from these pulses can be used to image the body tissue by measuring the relaxation properties of the excited atomic nuclei in the tissue. Pulsed gradient magnetic fields are used for spatial variation of static fields for image phase, frequency encoding, and slice selection within the body.

During imaging, the electromagnetic radiation produced by the MRI system may be picked up by implantable device leads used in implantable medical devices such as pacemakers or cardiac defibrillators. This energy may be transferred through the lead to the electrode in contact with the tissue, which may lead to elevated temperatures at the point of contact. The degree of tissue heating is typically related to factors such as the length of the lead, the conductivity or impedance of the lead, and the surface area of the lead electrodes. Exposure to a magnetic field such as a pulsed gradient magnetic field may also induce an undesired voltage in the lead.

SUMMARY

The present invention relates generally to the identification and cancellation of voltages induced on an implanted medical device located within a patient's body in the presence of a gradient magnetic field or other external noise. An illustrative system for identifying and cancelling magnetically-induced voltages on an implanted medical device having a lead implanted in or near the heart includes a reference model including one or more impedance parameters associated with the lead and of the body tissue within the patient's body, and a control unit adapted to control a voltage or current applied to the lead in the presence of a magnetic field. In some embodiments, the control unit is configured to dynamically control the voltage or current applied to the lead based on the one or more impedance parameters stored within the model. In use, and in some embodiments, the control unit is configured predict the variables (e.g., voltage or current) to be applied to the lead in the presence of the magnetic field in order to compensate for the effects of the field.

An illustrative method of dynamically controlling an implanted medical device located within a patient's body in the presence of a gradient magnetic field includes creating a model of the implanted lead and of body tissue within the body in the absence of a magnetic field, detecting the presence of a gradient magnetic field within the body, measuring the response of an excitation voltage or current applied to the lead in the presence of the gradient magnetic field, comparing the measured response against a modeled response obtained by the model in the absence of a gradient magnetic field, calculating the error between the measured response and the desired, modeled response, and modifying the voltage or current applied to the lead based on the calculated error to steer the measured response towards the desired response.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
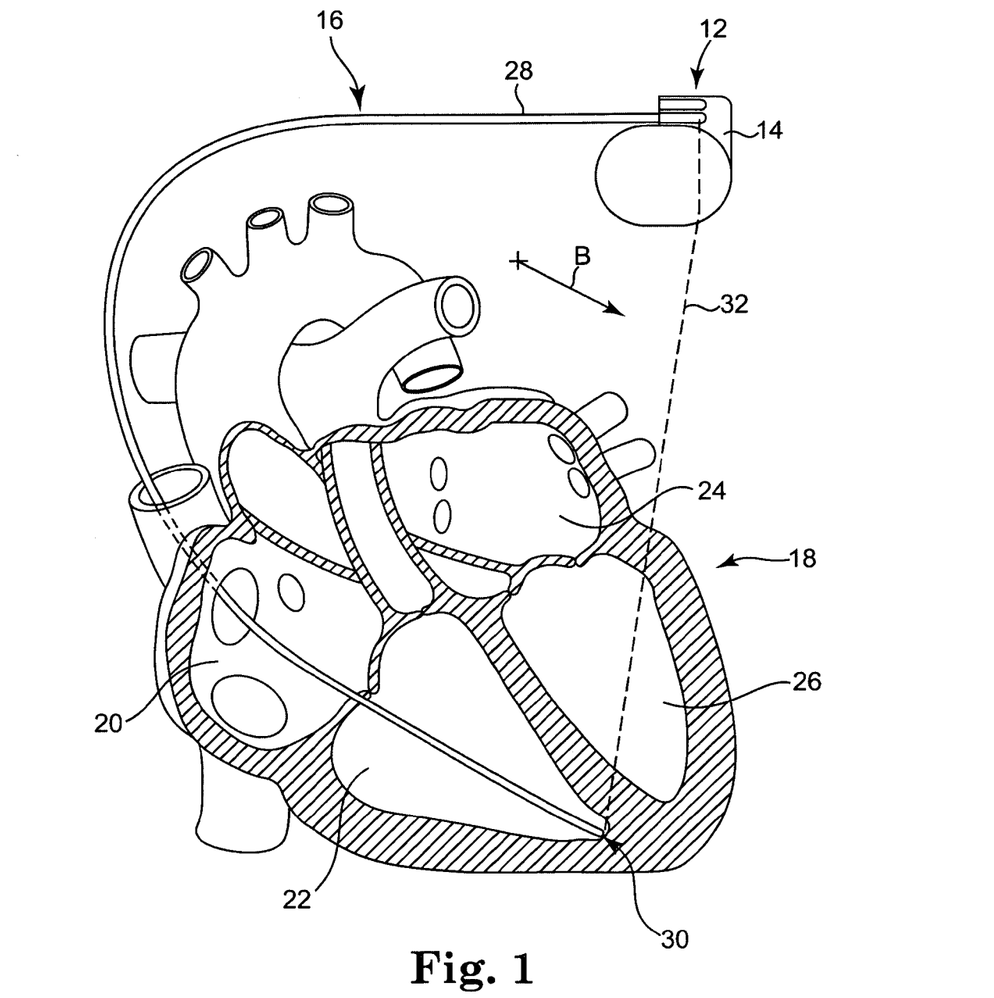
FIG. 1 is a schematic view of an illustrative medical device having a lead implanted within the body of a patient and subjected to a gradient magnetic field.

FIG. 1 is a schematic view of an illustrative medical device 12 equipped with a lead implanted within the body of a patient. In the illustrative embodiment depicted, the medical device 12 includes a pulse generator 14 implanted within the patient's body and a lead 16 (e.g., a unipolar or bipolar lead) placed at a location in or near the patient's heart 18. The heart 18 includes a right atrium 20, a right ventricle 22, a left atrium 24, and a left ventricle 26. The pulse generator 14 can be implanted subcutaneously within the body, typically at a location such as in the patient's chest or abdomen, although other implantation locations are possible.

A proximal portion 28 of the lead 16 can be coupled to or formed integrally with the pulse generator 14. A distal tip portion 30 of the lead 16, in turn, can be implanted at a desired location in or near the heart 18 such as the right ventricle 22, as shown. Although the illustrative embodiment depicts only a single lead 16 inserted into the patient's heart 18, in other embodiments multiple leads can be utilized so as to electrically stimulate other areas of the heart 18. In some embodiments, for example, the distal portion of a second lead (not shown) may be implanted in the right atrium 20. In addition, or in lieu, another lead may be implanted in or near the left side of the heart 18 (e.g., in the coronary veins) to stimulate the left side of the heart 18. Other types of leads such as epicardial leads may also be utilized in addition to, or in lieu of, the lead 16 depicted in FIG. 1.

During operation, the lead 16 can be configured to convey electrical signals from the pulse generator 14 to the heart 18. For example, in those embodiments where the pulse generator 14 is a pacemaker, the lead 16 can be used to deliver electrical therapeutic stimulus for pacing the heart 18. In those embodiments where the pulse generator 14 is an implantable cardiac defibrillator, the lead 16 can be utilized to deliver electric shocks to the heart 18 in response to an event such as a heart attack or ventricular tachycardia. In some embodiments, the pulse generator 14 includes both pacing and defibrillation capabilities.

When the pulse generator 14 is subjected to a gradient magnetic field, as shown generally by arrow "B" in FIG. 1, a magnetically-induced voltage ($V_{EMF}$) is delivered to the lead 16 that interferes with the therapeutic electrical signals delivered by the lead 16. During an MRI procedure, for example, a rapidly changing magnetic field B produced by an energized MRI coil induces an electromotive force voltage on the lead 16 that combines with the excitation voltage normally generated by the pulse generator 14. The voltage $V_{EMF}$ produced can be determined from Faraday's Law as follows:

$$V_{EMF} = \frac{dB}{dt} A$$

Thus, as can be understood from the above equation, the magnitude of the induced voltage $V_{EMF}$ is dependent on the time rate of change of the magnetic field $$\frac{dB}{dt}$$

and the effective area A upon which the gradient magnetic field acts.

For a unipolar lead 16 such as that depicted in FIG. 1, the effective area A upon which the gradient magnetic field B acts is defined generally as the area that is bounded by the length of the lead 16 from the proximal end 28 to the distal tip 30 and the distance from the lead tip 30 to the pulse generator 14. For a bipolar lead configuration, the effective area A upon which the gradient magnetic field B acts is typically less than for a unipolar lead, and is defined generally by the area between the tips of the lead electrodes. In either configuration, the voltage $V_{EMF}$ appears as a voltage source in the circuit loop 32 formed by the pulse generator 14, the lead 16, and the tissue impedance between the pulse generator 14 and the lead tip 30. This voltage $V_{EMF}$ induces a current on the lead 16 along with the desired therapeutic stimulus current generated by the pulse generator 14. During operation, this voltage $V_{EMF}$ can result in inappropriate currents on the lead 16 that are then transmitted into the surrounding cardiac tissue. The induced voltage $V_{EMF}$ may also result in device inhibition or inappropriate detections leading to charge timeout faults.

Figure 2:
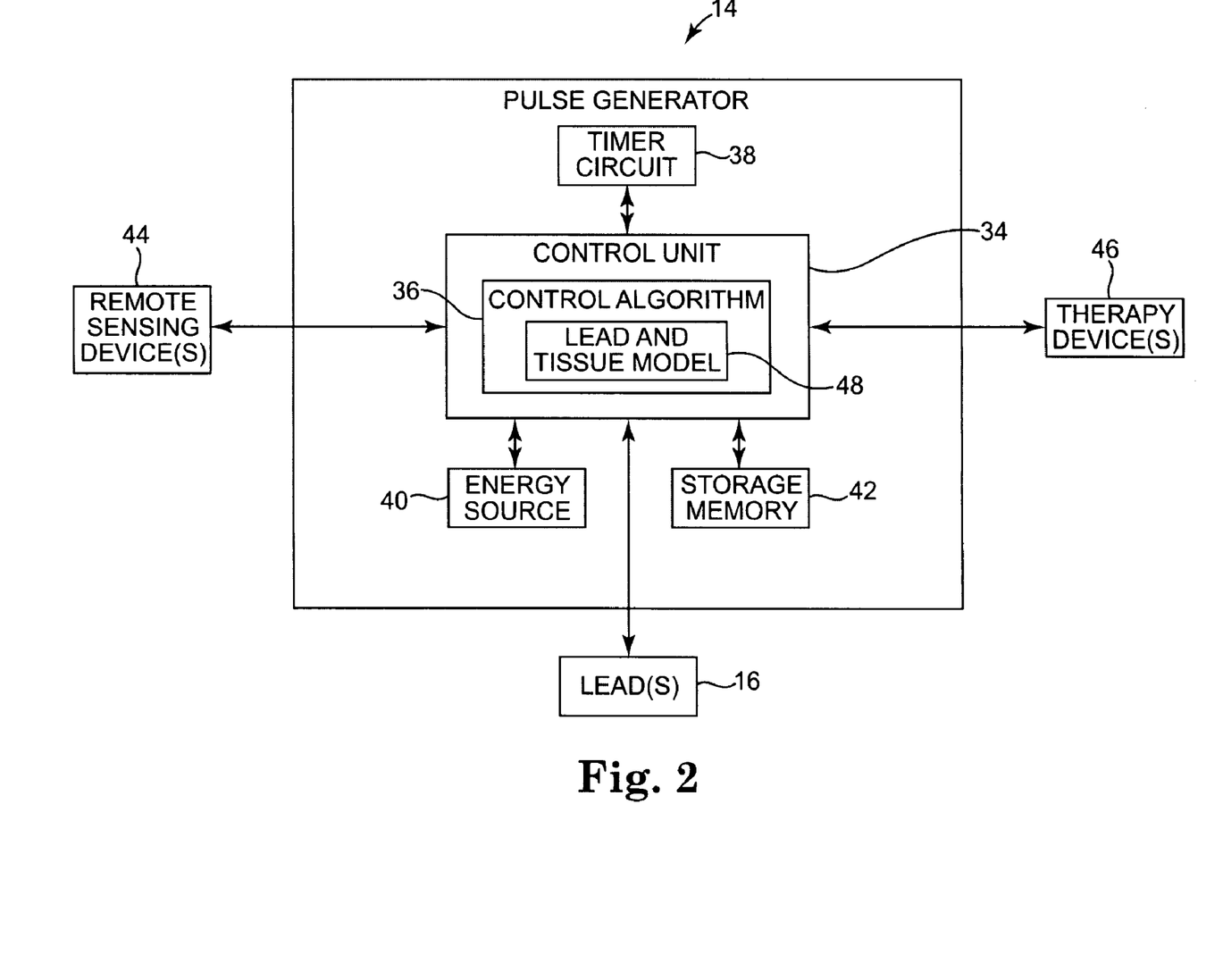
FIG. 2 is a block diagram showing several illustrative components of the pulse generator of FIG. 1.

FIG. 2 is a block diagram showing several illustrative components of the pulse generator 14 of FIG. 1. As shown in FIG. 2, the pulse generator 14 includes a control unit 34 adapted to run a control algorithm 36, which as discussed further herein, can be used to provide closed-loop control over the excitation voltage or current applied to the pulse generator lead 16 in the presence of a gradient magnetic field or other external noise. The control unit 34 can be coupled to other components of the pulse generator 14, including a timer circuit 38 for taking time and date measurements, an energy source 40 such as a rechargeable battery or power capacitor, and a storage memory 42 such as a flash memory or ferroelectric memory for storing data and commands used by the pulse generator 14.

The control unit 34 can further include control circuitry for controlling various other implantable medical devices coupled to the pulse generator 14, including one or more remote sensing devices 44 and/or therapy delivery devices 46. Examples of remote sensing 44 devices that can be coupled to the pulse generator 14 can include, but are not limited to, pressure sensors, accelerometers, pulmonary sound sensors, chemical sensors, and temperature sensors. In one embodiment, for example, the control unit 34 can be coupled to a magnetic sensor such as a reed switch or Hall-effect sensor that can be used to detect the presence of magnetic fields within the body.

In the illustrative embodiment of FIG. 2, the control algorithm 36 includes a lead and tissue reference model 48 used by the algorithm 36 to model one or more physical characteristics of the pulse generator lead 16 and the cardiac tissue adjacent to the lead 16. In some embodiments, for example, the reference model 48 includes an impedance parameter associated with the lead 16 as well as an impedance parameter associated with the cardiac tissue between the lead tip 30 and the pulse generator 14. In certain embodiments, the model parameters are stored as parameters within a look-up table or the like, and can be used by the control algorithm 36 to control the operation of the pulse generator 14, including the timing and magnitude of excitation voltage or current signals applied to the lead 16.

Figure 3:
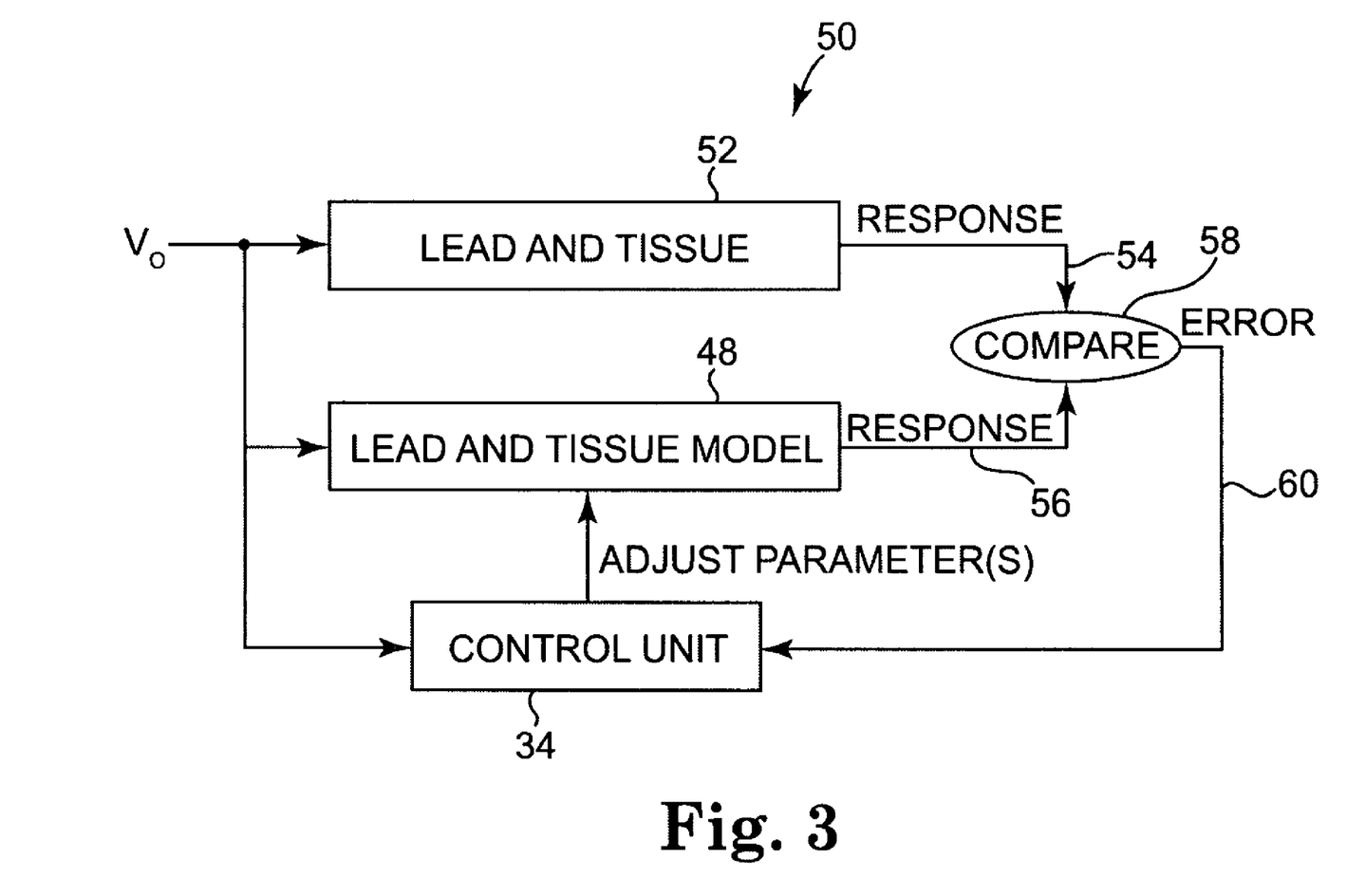
FIG. 3 is a block diagram showing an illustrative model-based system for modeling a medical device implanted within the body.

FIG. 3 is a block diagram showing an illustrative model-based system 50 for modeling an implanted medical device such as the pulse generator of FIG. 2. As shown in FIG. 3, an excitation voltage $V_0$ generated by the pulse generator 14 is applied to block 52, which represents the actual load characteristics of the lead 16 and the cardiac tissue. In the illustrative embodiment of FIG. 1, for example, the lead and tissue block 52 may represent the impedance of the lead 16 and the impedance of the cardiac tissue between the pulse generator 14 and the lead tip 30. In those embodiments in which a bipolar lead is used, the lead and tissue block 52 may represent the impedance of the cardiac tissue between the exposed portions of the electrodes.

In the absence of a gradient magnetic field, an accurate reference model 48 of the lead and cardiac tissue is developed based on one or more measured responses 54 from the lead and tissue 52. In some embodiments, for example, the reference model 48 may be generated by comparing via a comparator 58 a measured electrical current 54 from the implanted lead and body tissue 52 against a predicted electrical current 56 generated by the model 48 in the absence of a magnetic field. Measurement of the electrical current 54 within the lead 16 can be taken, for example, by a current sensor or by sensing a voltage drop across a reference resistor in series with the lead 16 and the body tissue.

Based on the responses 54,56 received from both the measured (i.e., actual) parameters and the model-based parameters, the comparator 58 outputs an error signal 60 indicating the error in the model's predicted response. This error signal 60 is then fed to the control unit 34, which updates one or more parameters in the model 48 to better simulate the actual lead and tissue impedance 52, thus reducing the model error. If, for example, the model 48 approximates a lead and tissue impedance that is greater than the actual, measured impedance, the control unit 34 may decrease the modeled impedance within the model 48 to minimize the error, similar to that performed by a closed-loop feedback controller such as a proportional-integral-derivative (PID) controller. Other suitable model parameter identification techniques including, but not limited to, least squares estimation (LS), maximum likelihood estimation (MLE), and best linear unbiased estimates (BLUE) may also be used to accurately calculate the model parameters.

The process of updating the model 48 to better approximate the actual lead and body tissue characteristics can be performed continuously, at predetermined time periods, or in response to a control signal from another device. In some embodiments, for example, the process of updating the model 48 can be accomplished initially when the lead is implanted within the body, and then subsequently at predetermined time intervals (e.g., every five minutes) until a static magnetic field is detected within the body, indicating the presence of a gradient magnetic field. In certain embodiments, model parameters such as the impedance of the lead 16 and the surrounding cardiac tissue, for example, can be updated by the control unit 34 by continuously or periodically measuring the voltage across a reference resistor coupled to the lead 16, and then comparing the measured voltage against a predicted current outputted by the model 48.

Figure 4:
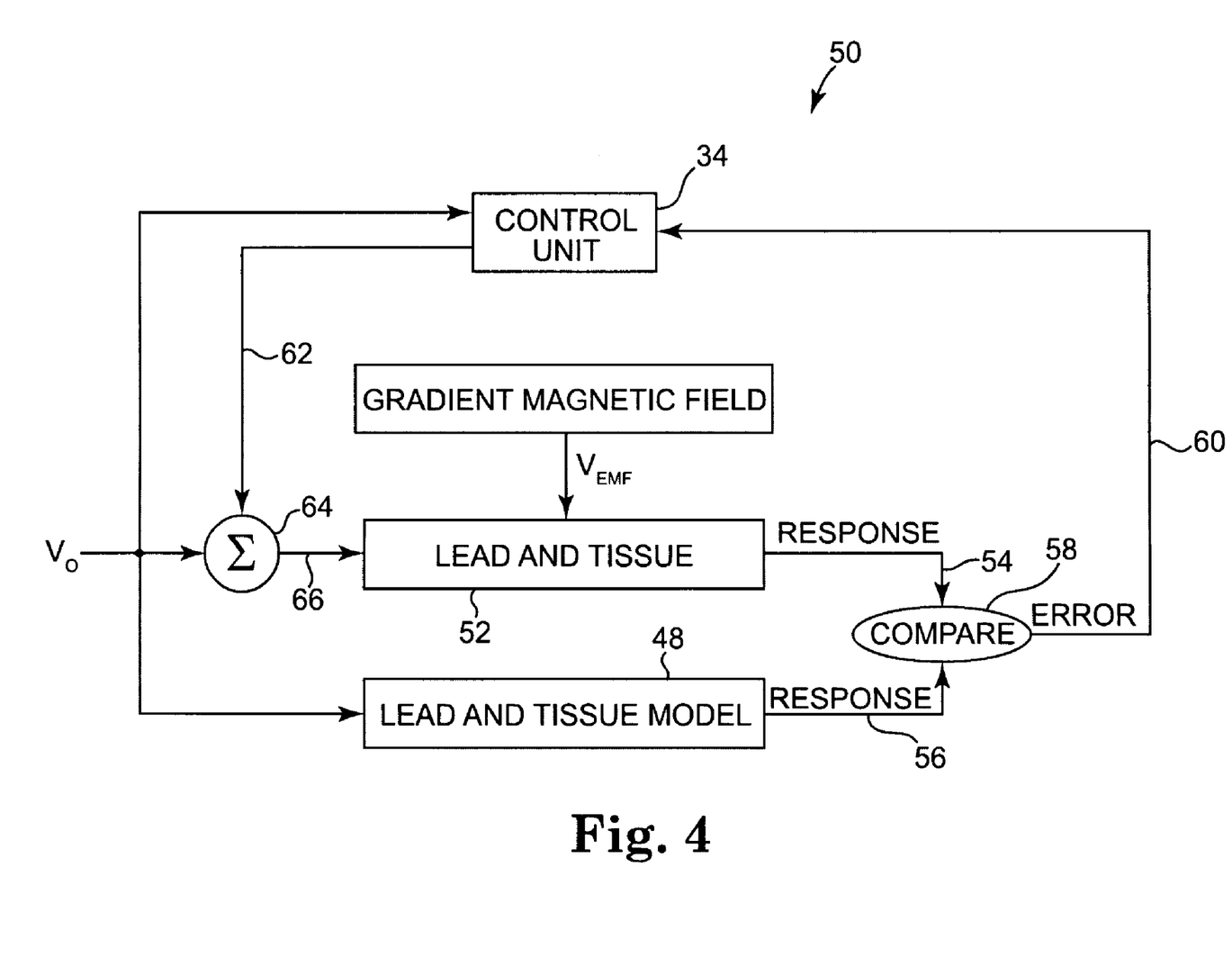
FIG. 4 is a block diagram showing the model-based system of FIG. 3 in the presence of a gradient magnetic field.

FIG. 4 is a block diagram showing the model-based system 50 of FIG. 3 in the presence of a gradient magnetic field. In some embodiments, the presence of a static magnetic field within the body during an MRI procedure can be detected by a magnetic sensor such as a Hall effect sensor, reed switch, or the like. From this sensed static magnetic field, the control unit 34 may then deduce that a gradient magnetic field is present within the body, activating an MRI mode within the control unit 34 to compensate for the induced EMF voltage $V_{EMF}$ at the pulse generator 14. Other techniques can also be used to determine the presence of the gradient magnetic field to activate the MRI mode within the control unit 34. In some embodiments, for example, a signal received from an external device in communication within the pulse generator 14 (e.g., from the MRI device) may signal the presence of the gradient magnetic field, causing the control unit 34 to enter into the MRI mode of operation.

In the presence of a gradient magnetic field, a magnetically-induced voltage $V_{EMF}$ produces a current that is transmitted through the lead and body tissue 52, which affects the measured response 54. In some cases, for example, the presence of the voltage $V_{EMF}$ may result in a greater amount of current within the lead than is desired for performing the therapy. This increase in response 54 is then compared against the response 56 predicted by the model 48 in the absence of the magnetic field to produce an error signal 60 that is fed to the control unit 34. In those embodiments where the actual and modeled responses 54,56 are currents, the error signal 60 may represent, for example, the magnitude of the difference between the actual current outputted by the lead and the predicted current outputted by the model 48.

Based on the error signal 60, the control unit 34 seeks to minimize the error between the actual lead and body tissue response 54 and the predicted (i.e., desired) response 56 generated by the model 48 in the absence of the magnetic field. In some embodiments, the control unit 34 then feeds a compensation voltage signal 62 to an adder 64, which is then added to the excitation voltage $V_0$ applied to the leads as voltage signal 66. In this manner, the control unit 34 dynamically modifies the voltage signal 66 applied to the lead and body tissue 52 so that the actual response 54 from the system 50 is similar to the modeled response 56 in the absence of the magnetic field. The output from the system 50 can be continuously compared with the measured responses 54 from the actual lead and body tissue 52, allowing the control unit 34 to maintain the error minimization between the model 48 and the lead and body tissue 52.

Figure 5:
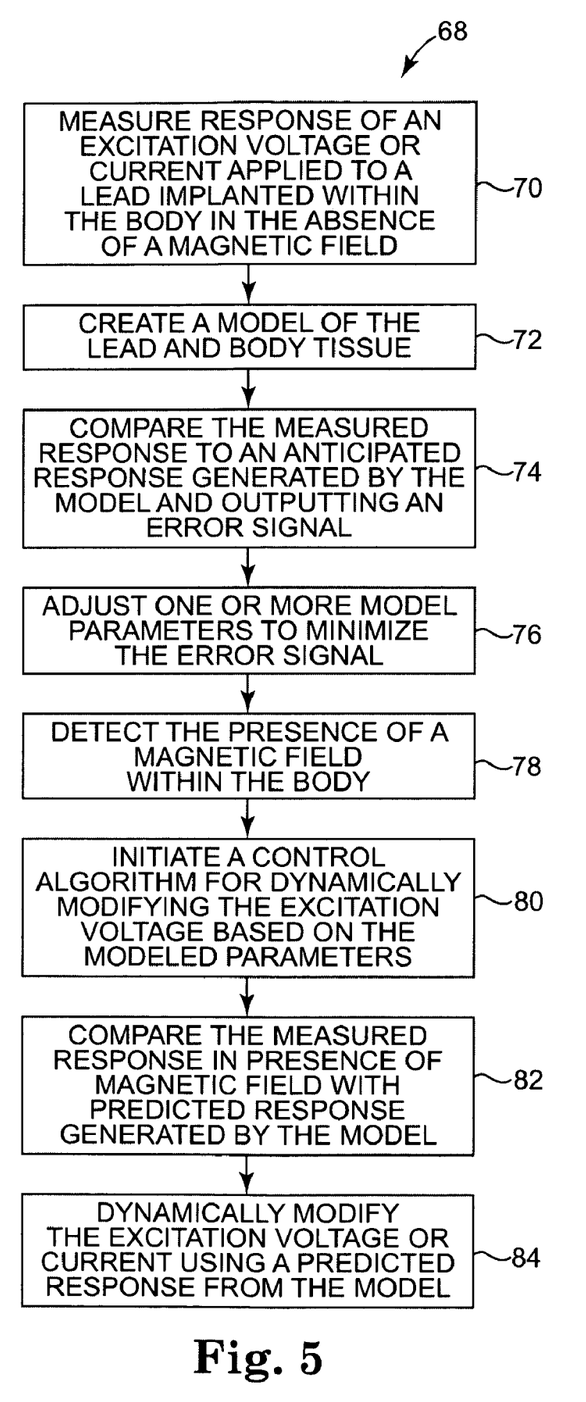
FIG. 5 is a flow chart showing an illustrative method of dynamically controlling an implanted medical device in the presence of a gradient magnetic field.

FIG. 5 is a flow chart showing an illustrative method 68 of dynamically controlling an implanted medical device in the presence of an external interference such as a gradient magnetic field. The method 68 begins generally at block 70 with the step of measuring the response of an excitation voltage or current applied to a lead implanted at a location within the body prior to the presence of a gradient magnetic field. In some embodiments, for example, measuring the response of the excitation voltage applied to the lead can include measuring the electrical current in the lead as a result of an excitation voltage generated by the pulse generator. Measurement of the electrical current within the lead can be accomplished, for example, by sensing the voltage across a reference resistor coupled to the lead, using a bridge circuit to sense the current within the lead, and/or by other suitable technique. From these measurements, the impedance characteristics of the implanted lead and body tissue are then determined.

From the measured response to the excitation voltage, one or more characteristics of the lead and body tissue are then analyzed to create a model of the lead and body tissue (block 72). In some embodiments, for example, the impedance characteristics of the lead and the body tissue are modeled based on one or more measured responses to an excitation voltage applied to the lead. The model may include, for example, an impedance parameter associated with the lead and an impedance parameter associated with the patient's heart.

Once a model is created representing the impedance of the implanted lead and body tissue, an anticipated response from the model resulting from the applied excitation voltage can then be compared against the actual, measured response produced by the excitation voltage to generate an error signal (block 74). The error signal can then be used by the control unit to adjust the model parameters to better approximate the actual, measured response from the implanted lead and body tissue in order to minimize the error signal (block 76). In some embodiments, for example, the model parameters can be continually or periodically adjusted by the pulse generator to minimize the error produced by the model, or to compensate for any changes to the lead and tissue impedance that occur over time.

The pulse generator can be configured to detect the presence of a magnetic field within the body (block 78), and then initiate a control algorithm within the control unit that dynamically modifies the voltage applied to the lead based on the parameters stored within the model (block 80). In some embodiments, for example, the pulse generator includes a sensor such as a Hall-effect sensor or reed-switch that can detect a static magnetic field or other external noise within the body produced by an MRI device, indicating the presence of a gradient magnetic field. The signal from the sensor can then be fed to the control unit, prompting the control unit to modify the voltage applied to the lead based on the model. In other embodiments, the pulse generator can be put into an MRI mode via a signal received from an external device (e.g., the MRI device), from another external device, or from another device implanted within the body.

Upon the detection of the magnetic field, the control unit can be configured to compare the actual response of the system in the presence of the magnetic field with the predicted response outputted by the model and determined in the absence of the magnetic field (block 82). Based on this comparison, an error signal is created which is then fed to the control unit for use in modifying the excitation voltage or current applied to the lead. In some embodiments, for example, the error signal may represent the magnitude of the difference between the current that is presently being applied to the lead and the current predicted by the model in the absence of the magnetic field. Based on the error signal, the control unit then seeks to minimize the error signal by dynamically modifying the voltage or current applied to the lead (block 84).

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A method of dynamically controlling an implanted medical device located within a patient's body in the presence of a magnetic resonance imaging (MRI) field, the method comprising:
   detecting the presence of an MRI field within the body;
   measuring the response of an excitation voltage or current applied to an implantable lead in the presence of the MRI field;
   comparing the measured response obtained in the presence of the MRI field with a predicted response outputted by a lead and tissue reference model, the model including one or more model parameters stored within a memory unit for modeling the lead and body tissue within the body; and
   dynamically modifying a voltage or current applied to the lead based at least in part on the predicted response outputted by the model.

2. The method of claim 1, wherein the lead and tissue reference model is formed by:
   measuring the response of an excitation voltage or current applied to the lead in the absence of an MRI field;
   comparing the measured response in the absence of the MRI field to a predicted response generated by the model and outputting an error signal; and
   adjusting one or more model parameters of the model to minimize the error signal.

3. The method of claim 1, wherein the implantable lead is a bipolar lead including a plurality of lead electrodes electrically coupled to a pulse generator, and wherein a the lead and tissue reference model comprises a model of the lead implanted within the heart and of the cardiac tissue disposed between the lead electrodes.

4. The method of claim 3, wherein the model includes one or more impedance parameters associated with the implanted lead and the cardiac tissue between the lead electrodes.

5. The method of claim 1, wherein the implantable lead is a unipolar lead including an electrode electrically coupled to a pulse generator, and wherein the lead and tissue reference model comprises a model of the lead implanted within the heart and of the body tissue disposed between the electrode and the pulse generator.

6. The method of claim 5, wherein the model includes one or more impedance parameters associated with the implanted lead and the body tissue between the electrode and the pulse generator.

7. The method of claim 1, wherein the lead and tissue reference model is formed in the absence of the MRI field.

8. The method of claim 1, wherein measuring the response of the excitation voltage or current includes measuring the current in the implanted lead.

9. The method of claim 1, wherein dynamically modifying the voltage or current applied to the lead based on the predicted response outputted by the model includes minimizing an error signal generated by comparing the measured response of the lead in the presence of the MRI field to a predicted response from the model determined in the absence of the MRI field.

10. The method of claim 9, wherein dynamically modifying the voltage or current applied to the lead based on the predicted response outputted by the model is performed by a control unit including a closed-loop feedback controller.

11. A method of dynamically controlling an implanted medical device located within a patient's body in the presence of a gradient magnetic resonance imaging (MRI) field, the method comprising:
    measuring the response of an excitation voltage or current applied to a lead implanted in or near the heart in the absence of a gradient MRI field;
    creating a model of the implanted lead and of body tissue within the body, the model including one or more impedance parameters stored within a memory unit for modeling the implanted lead and the body tissue within the body;
    comparing the measured response in the absence of the gradient MRI field to an anticipated response generated by the model and outputting an error signal;
    adjusting one or more of the model parameters to minimize the error signal;
    detecting the presence of a gradient MRI field within the body;
    measuring the response of an excitation voltage or current applied to the lead in the presence of the gradient MRI field;
    comparing the measured response obtained in the presence of the gradient MRI field with a predicted response outputted by the model; and
    modifying a voltage or current applied to the lead based at least in part on the predicted response from the model.

12. The method of claim 11, wherein the lead is a bipolar lead including a plurality of lead electrodes electrically coupled to a pulse generator, and wherein creating a model of the implanted lead and of body tissue includes creating a model of the lead implanted within the heart and of the cardiac tissue disposed between the lead electrodes.

13. The method of claim 12, wherein the one or more impedance parameters includes an impedance parameter associated with the implanted lead and an impedance parameter associated with the cardiac tissue between the lead electrodes.

14. The method of claim 11, wherein the lead is a unipolar lead including an electrode electrically coupled to a pulse generator, and wherein creating a model of the implanted lead and of body tissue includes creating a model of the lead implanted within the heart and of the body tissue disposed between the electrode and the pulse generator.

15. The method of claim 14, wherein the one or more impedance parameters includes an impedance parameter associated with the implanted lead and an impedance parameter associated with the body tissue between the electrode and the pulse generator.

16. The method of claim 11, wherein creating a model of the lead is performed in the absence of the gradient MRI field.

17. The method of claim 11, wherein measuring the response of the excitation voltage or current includes measuring the current in the implanted lead.

18. The method of claim 11, wherein dynamically modifying the voltage or current applied to the lead based on the predicted response outputted by the model includes minimizing an error signal generated by comparing the measured response of the lead in the presence of the gradient MRI field to a predicted response outputted from the model.

19. The method of claim 18, wherein dynamically modifying the voltage or current applied to the lead based on the predicted response outputted by the model is performed by a control unit including a closed-loop feedback controller.

\* \* \* \* \*